US008412328B2

(12) United States Patent
Whelan et al.

(10) Patent No.: US 8,412,328 B2
(45) Date of Patent: Apr. 2, 2013

(54) ELECTROMAGNETIC THERAPY DEVICE AND METHODS

(75) Inventors: Andrew J. Whelan, Frederick, MD (US); John Martinez, Houston, TX (US); Timothy Cox, Friendswood, TX (US); Stephanie Toy, League City, TX (US); James Woodhams, Murrieta, CA (US)

(73) Assignee: BioElectronics Corp., Federick, MD (US)

( * ) Notice: Subject to any disclaimer, the term of this patent is extended or adjusted under 35 U.S.C. 154(b) by 2257 days.

(21) Appl. No.: 10/442,448

(22) Filed: May 21, 2003

(65) Prior Publication Data
US 2004/0176805 A1    Sep. 9, 2004

Related U.S. Application Data

(63) Continuation-in-part of application No. 10/384,101, filed on Mar. 6, 2003, now Pat. No. 7,551,957.

(51) Int. Cl.
*A61N 1/00* (2006.01)
(52) U.S. Cl. ........................................................ 607/20
(58) Field of Classification Search ............. 607/50, 607/51, 65, 142, 152, 115, 149, 154, 155, 607/2, 9, 60, 20; 600/547; 320/127
See application file for complete search history.

(56) References Cited

U.S. PATENT DOCUMENTS

| 3,743,915 | A | * | 7/1973 | Struck ........................... 320/127 |
| 3,769,575 | A | * | 10/1973 | Rist et al. ...................... 324/329 |
| 4,412,540 | A | | 11/1983 | Bentall |
| 4,429,698 | A | | 2/1984 | Bentall |
| 4,471,787 | A | | 9/1984 | Bentall |
| 4,576,172 | A | | 3/1986 | Bentall |
| 4,611,599 | A | | 9/1986 | Bentall et al. |
| 4,688,580 | A | * | 8/1987 | Ko et al. ......................... 600/547 |
| 4,942,884 | A | | 7/1990 | Ichinomiya et al. |
| 5,478,303 | A | | 12/1995 | Foley-Nolan et al. |
| 6,317,630 | B1 | | 11/2001 | Gross et al. |
| 6,334,069 | B1 | * | 12/2001 | George et al. ...................... 607/2 |
| 2001/0044643 | A1 | * | 11/2001 | Litovitz ........................ 607/100 |

OTHER PUBLICATIONS

*Sports Injury Advisor*, Data sheet [on-line] Retrieved from the Internet Jul. 2, 2003 at URL: http://www.sportsinjuryadvisor.com.

* cited by examiner

*Primary Examiner* — George Manuel
(74) *Attorney, Agent, or Firm* — Fish & Richardson P.C.

(57) ABSTRACT

Systems and techniques for applying an electromagnetic field to bodily tissue include a self-contained and portable electromagnetic field generating device disposed over a surface of bodily tissue such that the radiated electromagnetic fields impinge upon the bodily tissue. The device includes an electromagnetic field generator, which is coupled to an antenna that is arranged to radiate the electromagnetic field. A power source is coupled to the generator to provide power for the device and an activator is used to initiate radiation of the electromagnetic field. Methods of inducing electrical current in bodily tissues and treating disorders, such as pain-related disorders, are also disclosed.

39 Claims, 7 Drawing Sheets

| Drawing of Location | Anatomical Description of Location |
|---|---|
| 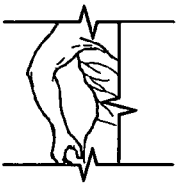 | Location at Elbow Area/Point:<br>At the External End of the Elbow Transverse Crease, When the Elbow is Flexed. |
|  | Location at Ankle Area/Point:<br>At the Depression at the Lower Border of the Malleolus Lateralis. |
| 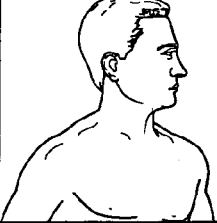 | Location at Shoulder Area/Point:<br>At 1" Below the Lateral Extremity of the Clavicle, at Level of the First Intercostals Space. |
| 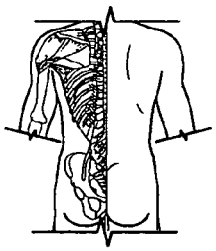 | Location at Low Back Area/Point:<br>Point 1: In Between 4th Lumbar Vertebra and 5th Lumbar Vertebra.<br>Point 2: 1" Apart to the Left from Point 1 Horizontally.<br>Point 3: 1" Apart to the Right from Point 1 Horizontally.<br>Point 4: 1.5" Above Point 2<br>Point 5: 1.5" Above Point 3 |
|  | Location at Knee Area/Point:<br>Point 1: In the Depression Anterior and Inferior to the Head of the Fibula.<br>Point 2: 1.5" Above the Medial Border of the Patella. |
| 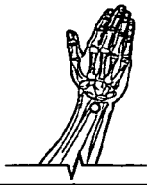 | Location at Wrist Area/Point:<br>In Between Radius and Palmaris Longus, or Where it Hurts the Most. |

FIG. 9

ELECTROMAGNETIC THERAPY DEVICE AND METHODS

CROSS REFERENCE TO RELATED APPLICATIONS

This application is a continuation-in-part and claims the benefit of priority from U.S. patent application Ser. No. 10/384,101, filed Mar. 6, 2003 now U.S. Pat. No. 7,551,957 and entitled "Electromagnetic Therapy Device and Methods," which is incorporated herein by reference in its entirety.

BACKGROUND

The following description relates to an electromagnetic field radiator that influences the metabolic characteristics of living systems. The techniques may be used to therapeutically promote healing of tissue and treat diseases.

Therapeutic value may be achieved by applying an electromagnetic field to injured bodily tissue. Application of a high-frequency electromagnetic field at a sufficiently low field strength so as not to produce tissue heating may result in a beneficial effect on healing of the tissue.

In some cases effectiveness of the therapeutic effect of the electromagnetic field may be improved by extending the duration of application of the field. The power requirements of the applied field may be reduced and the effectiveness of the treatment increased by extending the treatment duration.

SUMMARY OF THE DISCLOSURE

The present application teaches systems and techniques for applying an electromagnetic field to bodily tissue.

In one aspect, a device for applying a therapeutic electromagnetic field is disclosed including an electromagnetic field generator, which is coupled to an antenna that is arranged to radiate the electromagnetic field. A power source is coupled to the generator to provide power for the device and an activator is used to initiate radiation of the electromagnetic field. The therapeutic device is self-contained and portable and is disposed over a surface of bodily tissue such that the radiated electromagnetic field impinges upon the bodily tissue.

In an implementation, the power source is a battery of less than approximately 10 VDC.

In another implementation, the device is a component of a therapeutic delivery system. The therapeutic delivery system includes a member from the group of a patch, a bandage, a pad, a brace, a strap, tape, adhesive and a cast.

In another aspect, a technique for applying a therapeutic electromagnetic field is facilitated by incorporating a power source, antenna and electromagnetic field generator within a portable and disposable package and affixing the device to bodily tissue. The device generates an electromagnetic field that induces an alternating current in the bodily tissue. In another implementation, the average available radiated power is less than approximately 1 milliwatt and the peak available radiated power density is less than 100 microwatts per square centimeter measured substantially at the surface of the tissue.

Some implementations of the systems and techniques described herein may provide one or more of the following advantages. The device may be suitable for prolonged use. The self-contained unit can encourage patient compliance. In some implementations the device may be placed directly over bodily tissue to provide electromagnetic therapy to the tissue. The device may be part of a therapeutic agent delivery system such as a patch, bandage, pad, brace, cast, or other tissue injury support device.

In another aspect, a method is disclosed for inducing electrical current in a bodily tissue by: (1) positioning a device described herein adjacent a bodily tissue of an individual; and (2) operating the device for a duration, at a frequency, and at a peak available radiated power density effective to induce electrical current in the bodily tissue, wherein the device is positioned relative to the individual such that the device induces electrical current in the bodily tissue without making conductive contact with the bodily tissue. In some embodiments, the induction of electrical current in the bodily tissue reduces or eliminates a pain sensation in the individual.

In another aspect, a method is disclosed for treating an individual by: (1) positioning a device described herein adjacent a bodily tissue of an individual; and (2) operating the device for a duration, at a frequency, and at a peak available radiated power density effective to elicit a therapeutic response in the individual, wherein the device is positioned relative to the individual such that the device induces electrical current in a bodily tissue of the individual without making conductive contact with the bodily tissue.

In another aspect, a method is disclosed for treating an individual by: (1) providing a device containing an electromagnetic field generator; (2) positioning the device adjacent a bodily tissue of an individual; and (3) operating the device for a duration, at a frequency, and at a peak available radiated power density effective to elicit a therapeutic response in the individual, wherein the device is positioned relative to the individual such that the device induces electrical current in the bodily tissue of the individual without making conductive contact with the bodily tissue, and wherein the device effects a penetration of the induced current into the bodily tissue such that the therapeutic response is elicited at a depth of at least 2 cm in the bodily tissue. In some embodiments, the therapeutic response is elicited at a depth of at least 3, 4, 5, or 6 cm in the bodily tissue. In other embodiments, the therapeutic response is elicited at a depth of 2 to 3, 2 to 4, 2 to 5, 2 to 6, 3 to 4, 3 to 5, or 3 to 6 cm in the bodily tissue.

In another aspect, a method is disclosed for treatment by: (1) providing a device selected from the group consisting of a pulsed electromagnetic field therapy (PEMF) apparatus, a transcutaneous electrical neural stimulator, and a static magnet array; (2) positioning the device at a distance from an individual effective to elicit a therapeutic response in the individual, wherein the device is positioned at a bodily location selected from the group consisting of the external end of the elbow transverse crease, the depression at the lower border of the malleolus lateralis, below the lateral extremity of the clavicle at the level of the first intercostals space, between the fourth lumbar vertebra and the fifth lumbar vertebra or 1 inch to the right or left thereof horizontally, a depression anterior or inferior to the head of the fibula, about 1.5 inches above the medial border of the patella, and between the radius and the palmaris longus; and (3) maintaining the device at the bodily location for a duration effective to elicit the therapeutic response.

In the methods described herein, positioning a device adjacent to a bodily tissue of an individual refers to placing the device close to the skin of the individual (e.g., within 0.5, 1, 2, 3, 4, 5, or 6 inches of the skin) or in contact with the skin. The device can be encapsulated in a material and still be considered adjacent to a bodily tissue, so long as it operates in the manner described herein. The methods do not entail penetration of the skin by the device and/or the application of electrodes to the skin (e.g., the device induces current in a bodily tissue in the absence of an application of electrodes to the skin). Tissues that can receive the electrical current according to the methods described herein include, for example, the skin as well as tissues that underlay the skin (e.g., joints or bones).

An exemplary device for use in the methods described herein comprises: an electromagnetic field generator; an antenna coupled to the generator and arranged to radiate the electromagnetic field; a power source (e.g., a battery) coupled to the generator; and an activator to initiate radiation of the electromagnetic field, wherein the device is self-contained and portable. The antenna can optionally contain antenna conductors on a printed circuit board. In some embodiments, the device additionally contains: an annular ring to surround the battery; and a wire wound around the annular ring. In some embodiments, the annular ring has a stepped cross-section and a wire wound on a top and outer side of the annular ring coupled to the antenna conductors. In some embodiments, the annular ring contains a ferrite ring. In some embodiments, the annular ring contains an insulating-magnetic ring.

The current induced in the bodily tissue of an individual can be, for example, parallel or perpendicular to the direction of antenna conductors.

In some embodiments of the methods described herein, the frequency is 27±0.5 MHz (e.g., 27.1 MHz).

In some embodiments of the methods described herein, the peak available radiated power density is less than 100 microwatts per square centimeter measured at the surface of the bodily tissue (e.g., the skin of the individual).

The device used in the methods can optionally contain a delivery system, e.g., a patch, bandage, pad, brace, strap, tape, adhesive, or cast. In some embodiments the delivery system is a single use adhesive bandage.

The methods described herein can additionally include pulsing the generated electromagnetic field. In addition, the methods can also include altering at least one of a duty-cycle and a pulse repetition rate of the pulsed electromagnetic field. In some embodiments, the duty cycle is approximately 8%-10%.

In some embodiments, the individual has a pain-related disorder and the therapeutic response includes a reduction or elimination of pain in the individual. Examples of pain-related disorders include, for example, pain response elicited during tissue injury (e.g., inflammation, infection, and ischemia), pain associated with musculoskeletal disorders (e.g., joint pain such as that associated with arthritis, toothache, and headaches), pain associated with surgery, pain related to irritable bowel syndrome, and chest pain.

In some embodiments, the individual has a disorder selected from the group consisting of adhesive capsulitis, tennis elbow, osteoarthritis, back pain, multiple sclerosis, tendon inflammation, and carpal tunnel syndrome, and the therapeutic response includes a reduction or elimination of pain associated with the disorder.

In some embodiments, the individual has a bone, joint, soft-tissue, or connective tissue disorder and the therapeutic response includes a reduction or elimination of inflammation in a bone, joint, soft-tissue, or connective tissue of the individual. In some embodiments, the individual has a bone, joint, soft-tissue, or connective tissue disorder and the therapeutic response includes a reduction or elimination of pain associated with the disorder.

In some embodiments, the individual has a dental condition, and the therapeutic response includes a reduction or elimination of pain associated with the condition.

In some embodiments, the individual has an arthritic disorder and the therapeutic response includes a reduction or elimination of pain associated with the disorder. In an example, the disorder is osteoarthritis of the knee and the therapeutic response includes a reduction or elimination of pain of the knee.

Details of one or more implementations are set forth in the accompanying drawings and the description below. Other features and advantages will be apparent from the description and drawings, and from the claims.

BRIEF DESCRIPTION OF DRAWINGS FIG. 1 is an implementation of a therapeutic electromagnetic device depicting an arrangement of the components.

Figure 4A:
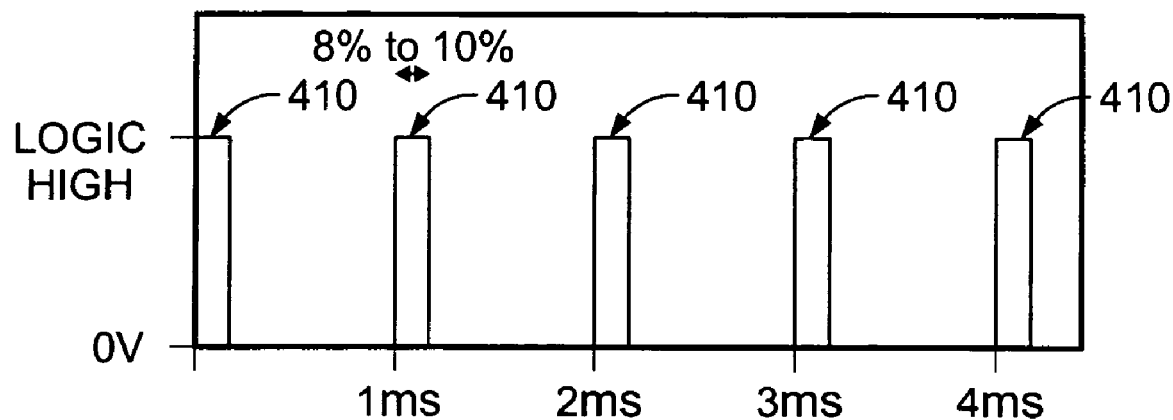
Figure 4B:
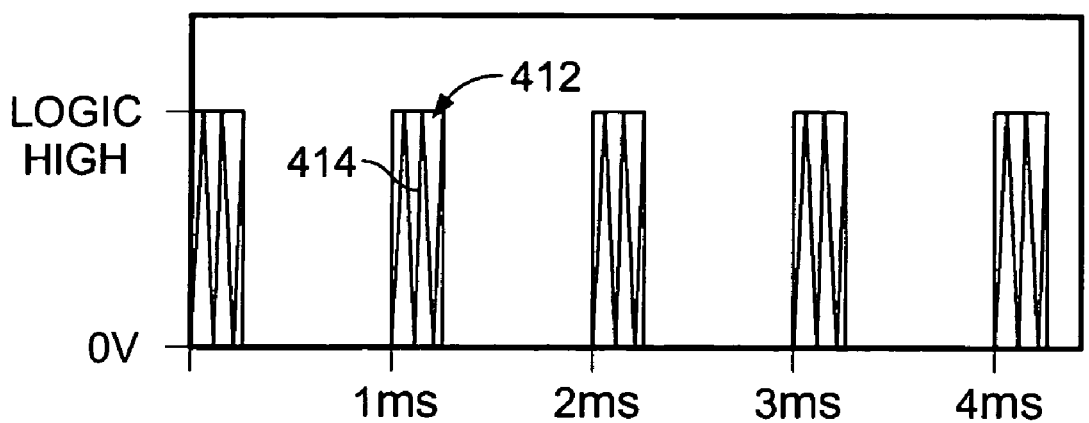
Figure 5A:
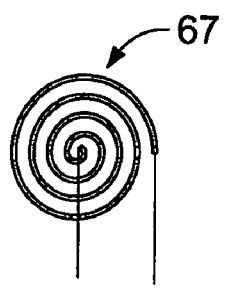
Figure 5B:
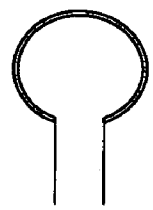
Figure 5C:
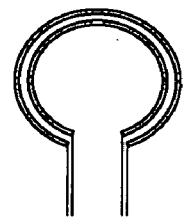
Figure 5D:
Figure 5E:
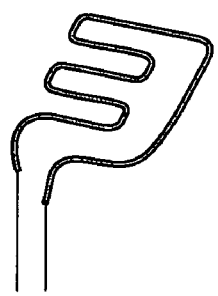
Figure 5F:
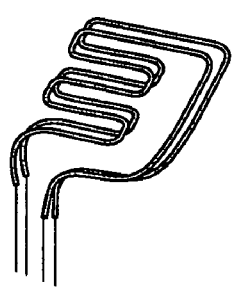
Figure 5G:
Figure 5H:
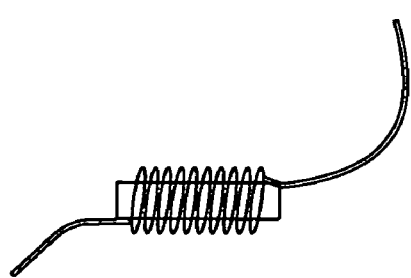
Figure 5I:

FIGS. 4A-B illustrate a control waveform and resulting RF waveform.

FIGS. 5A-I illustrate alternative antenna configurations.

Figure 6:
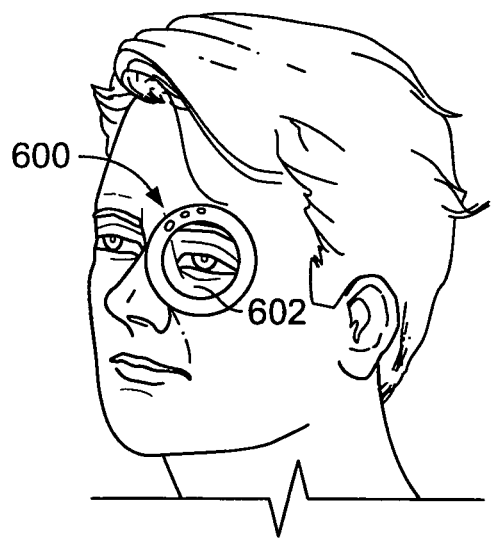

FIG. 6 depicts an alternative configuration of a therapeutic electromagnetic device.

FIGS. 7A-D depict various applications of a therapeutic electromagnetic device.

Figure 8:
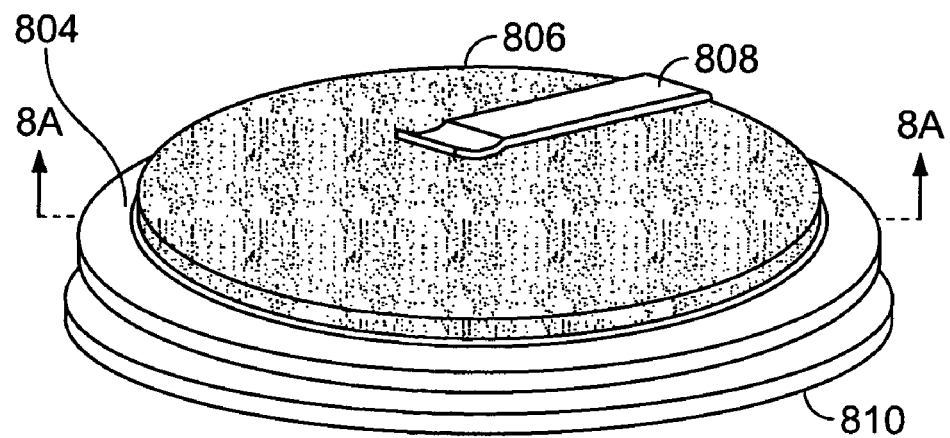
Figure 8A:
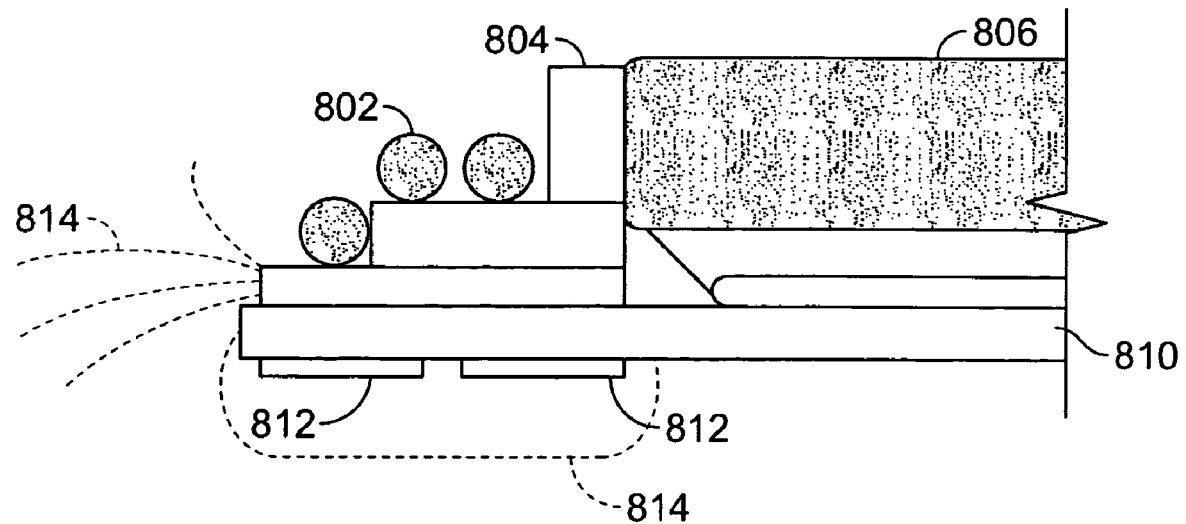

FIG. 8 is an implementation of an enhanced antenna.

FIG. 9 depicts anatomical locations for placement of a therapeutic device.

Like reference symbols in the various drawings indicate like elements.

DETAILED DESCRIPTION

The systems and techniques described here relate to promoting therapeutic healing of tissue, providing prophylaxis for, and treatment of disorders and diseases through the application of an electromagnetic field. The techniques include providing a self-contained miniaturized electromagnetic field generating device that may be applied to bodily tissue. In some implementations the techniques and systems include devices that are disposable and portable.

The generated electromagnetic field can induce alternating current in bodily tissue. The alternating current may be subjected to non-linear electrical characteristics (for example, diode-like rectification) and so generate low frequency electrical potentials having a time dependence the same as the pulse modulation. The low frequency electrical potentials may stimulate cellular communication by, for example, altering the frequency of cellular activation potentials. Cellular communication may promote the healing of inflammation and the reduction of edema.

These techniques also may provide a method of transmission and utilization of the body's capacitance by affixing a transmitting element of the device to conform and fit closely over the bodily tissue, provide a small space and low weight device for field transport and emergency use. Patient compliance with a therapeutic regimen may be important to promote healing of bodily tissue. Patient compliance may be improved by providing a therapeutic device that is self-contained and portable.

Some or all of the components of a therapeutic electromagnetic energy delivery device may be integrated into a control circuit chip to miniaturize the device. The device may be affixed to various parts of the body for prolonged electromagnetic therapy. Patient compliance to the therapeutic regimen may be improved by embedding or concealing the device into a patch, bandage, pad, wrap, brace, cast, or other injury support device and affixed to the body or taped over the bodily tissue.

The effectiveness of electromagnetic therapy may be improved by extending the treatment duration. Lower power electromagnetic radiation may be applied for a longer period of time than may be necessary for shorter periods of application. The self-contained unit disclosed may promote patient compliance with periods of therapy that may extend over weeks.

Figure 1:
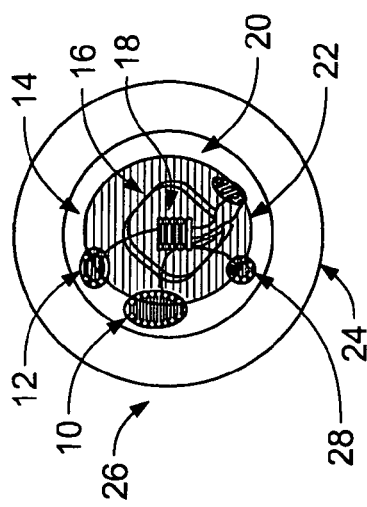

FIG. 1 illustrates an implementation of a therapeutic electromagnetic device 26. A control circuit chip 18 may provide the functionality for the therapeutic electromagnetic device to operate. An implementation of a control chip 18 is disclosed in association with the description of FIG. 3 and includes a radio frequency (RF) generator. A power source 10 coupled directly or indirectly to the control chip may be used to power the therapeutic electromagnetic device. The power source may include a battery, photovoltaic cell or an electro-chemical cell. An activator 12 is used to activate the device. The activator may include a switch that is a single-use or multiple use type and may be momentary or alternate-action. Actuation of the activator may be accomplished in various ways including by use of pressure, light or electronic signal either remotely or proximately. An antenna 16 is used to emit electromagnetic radiation and a deflector shield 14 may be used to deflect the electromagnetic radiation to the bodily tissue. In an implementation, the antenna 16 and/or deflector 14 may be tuned for electromagnetic energy in the frequency range of 27±0.5 Mhz. The therapeutic electromagnetic device also may include a tuning coil 20 which may be used to match the impedance of the antenna 16 to the RF signal generator within the control circuit chip 18. A circuit board 22 may be used to mount the elements of the device and, in some cases, provide coupling between the elements of the device. The circuit board may be comprised of a rigid or flexible material. The assembled device weighs less than 12 grams.

In some implementations, an adhesive material 24 may be used for affixing the therapeutic electromagnetic device to bodily tissue. Adhesive material 24 includes, for example, pharmaceutical grade adhesives. The therapeutic electromagnetic device may be affixed using other single or multiple usage therapeutic delivery devices, which include a patch, a bandage, a pad, a brace, a strap, tape, adhesive and a cast. In some implementations, an indicator 28 can be used to provide indicia that the therapeutic electromagnetic device is active. The indicator 28 may include one or more of the following: a visual indicator such as a light emitting diode (LED), lamp or electro-luminescent display; an auditory indicator such as noise generator; or a tactile indicator such as a vibrator. In an implementation, the indicator may be coupled to an electromagnetic field detector in the control circuit chip 18 and indicate the presence or lack of electromagnetic radiation from the device. In various implementations the indicator may be steady, intermittent or pulsed.

The therapeutic electromagnetic device may be enclosed or encapsulated in encapsulants or other potting compounds to reduce the vulnerability of the device to foreign materials including moisture, fluids, fungus, static charges, dirt, particulate matter and dust. The encapsulants, including insulating resins such as epoxies, polyurethanes, and polyesters, may be cast into cavities containing the device components, to insulate, protect, and hold the components in place. The encapsulant also may reduce the vulnerability of the device to environmental factors including air, heat, sunlight, ultraviolet light and spurious electromagnetic fields. In some implementations, a conformal coating may be applied to the device components and couplings to reduce the vulnerability of the device to moisture, fluids, fungus, static charges, dirt, particulate matter and dust.

Figure 2:
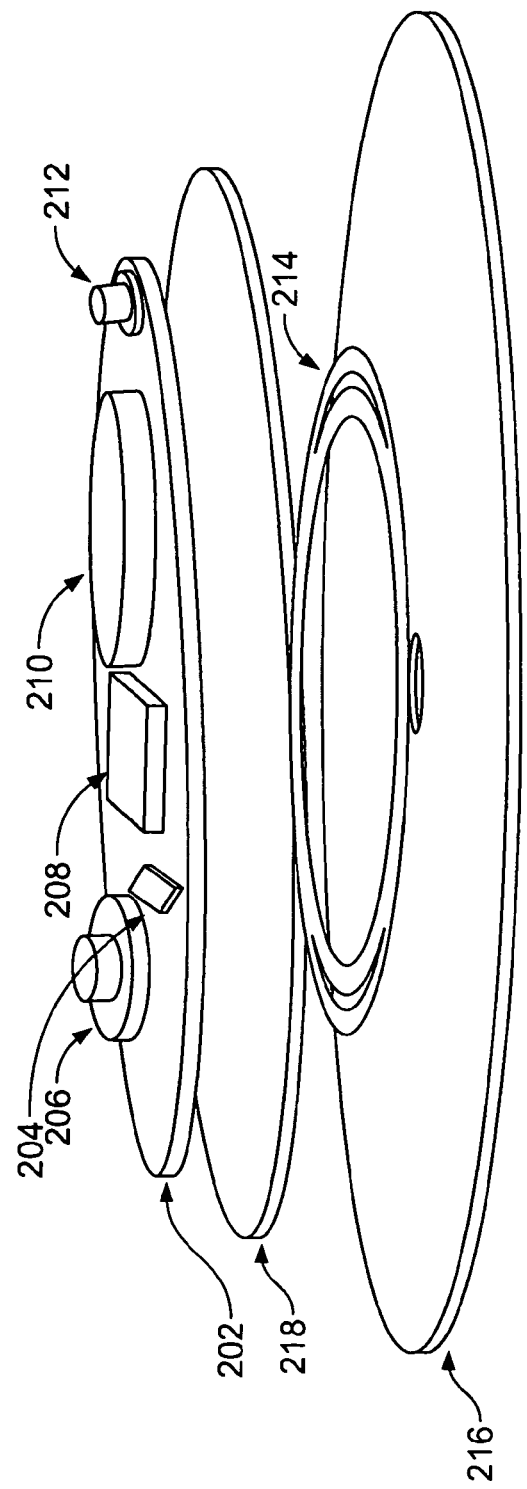
FIG. 2 is an implementation of a therapeutic electromagnetic patch depicting components in layers.

FIG. 2 illustrates an exploded view of an implementation of the therapeutic electromagnetic device having the components in a layered form. An activation switch 206, a control circuit chip 208, a power source 210, a visual indicator 212 and a tuning coil 204 may be mounted on a top layer and attached to a circuit board 202 to provide coupling between the components. A deflecting shield 218 may be layered under the circuit board 202. Or deflecting shield is a layer or coating of material, having high magnetic permeability, applied directly to circuit board 202. An antenna 214 to radiate electromagnetic energy may be layered under deflecting shield 218 and coupled to the circuit board 202. The deflecting shield 218 may deflect some of the energy radiated from the antenna 214 away from components mounted on the circuit board and toward the bodily tissue. The shape of the antenna is not restricted and some common shapes are depicted in FIGS. 5A-I. The antenna may also comprise separate conductors that do not make electrical contact with each other. In some implementations, the antenna may have a thickness of less than 5 millimeters and diameter of less than 9 centimeters or in other implementations, a length of less than 27 centimeters. The antenna may be incorporated into the circuit board 202.

The shape of the circuit board 202 and deflecting shield 218 may be altered to adapt the therapeutic device to particular applications. The thickness of the device is less than 10 millimeters. In one implementation, an adhesive material 216 such as a pharmaceutical adhesive may be mounted to the bottom layer under antenna 214 to adhere the device to bodily tissue. Other therapeutic delivery devices including a patch, a bandage, a pad, a brace, a strap, tape, adhesive and a cast also may be used. In some implementations, the components may be selected and arranged for specific applications. Referring to FIG. 6, for example, the therapeutic device 600 may have a generally annular shape in a therapeutic application such as post-operative healing over an eye or breast. In this case, the annular shape defines a hole 602 through which a patient may see while the device is in place.

Figure 3:
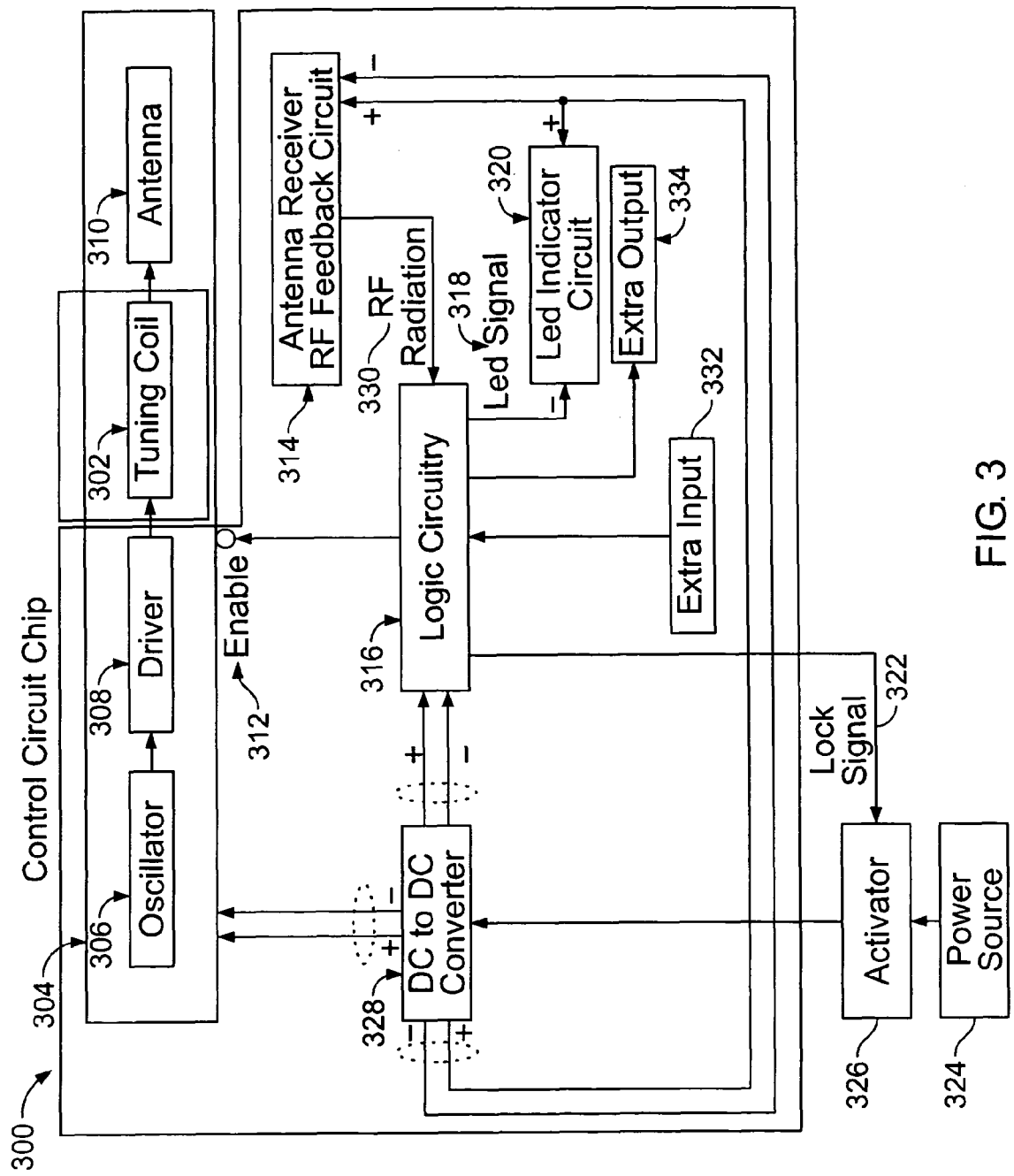
FIG. 3 is a block diagram of an implementation of a therapeutic electromagnetic device.

FIG. 3 is a block diagram of the circuitry of one implementation of a control circuit chip 300 used in a therapeutic electromagnetic device. Optionally, a tuning coil 302 may be included within the control circuit chip 300 or mounted separately. The components of the control circuit chip 300 may be integrated into one part or may be assembled from discrete components. The control circuit chip 300 includes an electromagnetic field generator 304 comprised of an oscillator 306 and a driver 308. Logic circuitry 316 coupled to the generator 304 provides an enable signal 312 to the generator 304. The logic circuitry also may provide an LED signal 318 to an indicator circuit 320, which, in turn, may be coupled to an indicator (not shown). Logic circuitry 316 may include discrete components, a programmable logic device (PLD), a microprocessor or other micro-controller unit (MCU). A power source 324 may be used to supply power to the electromagnetic therapy device. An activator 326 controls the flow of power from the power source to a DC to DC converter 328. The activator includes a switch that can provide for a one-time activation and then sustain activation for the duration of life of the power source. The DC to DC converter 328 provides power to the control chip components including the logic circuitry 316, the electromagnetic field generator 304 and an optional RF feedback circuit 314. The RF feedback circuit provides an RF radiation signal 330 to the logic circuitry 316. The logic circuitry also may provide an LED signal 318 to an LED indicator circuit and a lock signal 322 to the activator 326.

The electromagnetic field generator 304 comprises an oscillator 306 to generate an electromagnetic field, a driver circuit 308 to receive the electromagnetic field, amplify the wave and to provide the amplified wave to the optional tuning coil 302. The tuning coil 302 may be used to match the impedance of the driver 308 to an antenna 310, which is arranged to radiate the amplified electromagnetic energy. The oscillator 306 may be arranged to produce electromagnetic waves, including sinusoidal waves, at a carrier frequency of 27±0.5 megahertz (MHz). In an implementation, the electromagnetic therapeutic device has an average available power of less than approximately 1 milliwatt and a peak available radiated power density of less than 100 microwatts per square centimeter ($\mu W/cm^2$) measured substantially at the surface of the tissue. The electrical efficiency of average available radiated power generation also may be greater than 20%. Average available power is the power that the device can dissipate into a resistive load. The average available power is distinguished from the power of the carrier within each pulse, which is termed the "peak" power. The peak available radiated power density is the maximum carrier wave power as if it was continuous and not pulsed, divided by the loop area of the antenna. A high voltage generator (not shown) may be included to increase the intensity of the radiated field. The high voltage generator may produce less than 30 VDC and may be synchronized to allow energy transforming action between therapy pulses, so that therapy pulses are not affected by the energy transformation action. Energy transformation could comprise connecting the battery to an inductive coil for a brief duration, and then switching the coil into a diode or rectifier and capacitor. The capacitor accumulates charge at a higher voltage than the battery. When voltage on the capacitor reaches a predetermined value, the capacitor may be discharged into the frequency generator for producing a therapy pulse. Alternatively, a transformer connected to a rectifier and capacitor as a flyback transformer may replace the inductive coil.

The enable signal 312 may be used to initiate or curtail radiation of the electromagnetic energy. The RF feedback circuit 314 is arranged to detect RF radiation from the antenna 310 and to provide RF radiation signal 330 to logic circuitry 316. Based on the level of the RF radiation signal 330, the logic circuitry provides the LED signal 318 to enable/disable the LED indicator circuit 320, which drives the indicator (not shown) and provides an indication that the antenna is radiating electromagnetic energy. The logic circuitry 316, the LED indicator circuit 320 or the indicator may be arranged so that the indicator is either indicating continuously, intermittently or pulsating. The logic circuitry also may provide the enable signal 312 to enable/disable the electromagnetic field generator 304.

In an embodiment, the energy radiated by the antenna 310 may be pulsed. PEMF may be used to provide electromagnetic field therapy over long periods of time and reduce heating of the bodily tissue. FIG. 4A illustrates that an enable signal 410 that may be provided from the logic circuit 316 to enable the generation and radiation of electromagnetic energy. In this example, the enable signal goes to a logic level high every millisecond. The enable pulse level is shown as a logic high but alternatively may be a logic low. In some implementations, the logic high level may be the power source, or regulated non-zero, voltage although other voltages are possible. The illustrated duty cycle is approximately 8% to 10%. In some implementations, the electromagnetic therapeutic device may operate in the frequency range of 3-30 MHz and application of the electromagnetic energy may be pulsed to maximize the therapeutic effect of the field. Pulses of 100 microsecond ($\mu S$) pulse duration at intervals of 1 millisecond (mS) (a pulse repetition rate of 1000 Hz) may be preferable. In order to reduce heating of the tissue, the electromagnetic field strength may be limited to less than 100 micro-Watts per square centimeter ($\mu Wcm-2$) as measured proximate the surface of the tissue. FIG. 4B illustrates a resulting output 412 from the antenna. The electromagnetic field 414 is radiated from the antenna only when the enable signal 410 is at a logic high.

Referring again to FIG. 3, the power source 324 may be direct current (DC) and preferably less than approximately 10 VDC. The power source may be rechargeable. The rechargeable power source may be a battery of the lithium metal hydride or lithium ion or lithium polymer technology that may be recharged from an external source, including a sine wave field generator proximate the antenna 310 or separate coil (not shown) for the non-contacting induction of power from the external source into the therapeutic device. Current induced in the antenna or separate coil may be rectified and supplied as a reverse current to the rechargeable power source until the power source reaches a predetermined terminal voltage or case temperature.

The power source 324 is coupled to the activator 326. When the activator is actuated, power is coupled to the DC to DC converter which may boost and regulate the power source voltage level. Regulated output voltage from the DC to DC converter 328 is supplied to the logic circuitry 316, electromagnetic field generator 304 and RF feedback circuit 314. A lock signal 322 may be provided by the logic circuitry 316 to lock the activator in the "on" position when the activator is actuated at least once.

Optionally, extra input signals 332 and extra output signals 334 may be received and/or provided by the logic circuitry 316 for additional functionality. For example, an output signal may be provided that provides indicia of the level of the voltage level of the power source 324. The output signal may activate a visual or auditory alarm when the power source requires replacement. An output signal may be provided that provides indicia of a state of the bodily tissue. The electrical permittivity and conductivity of tissue affects the frequency of the carrier wave in the device. The ratio of conductivity ($\sigma$) to permittivity multiplied by angular frequency ($\omega \epsilon$) determines the polarity of the frequency change. If $\sigma$ exceeds $\omega \epsilon$ then the carrier frequency decreases. If $\omega \epsilon$ exceeds $\sigma$ then the carrier frequency increases. As conductivity is related to pH and free ion concentration, while permittivity is related to abundance of polar molecules and cell membrane charge, the bioelectrical state of the tissue may be assessed by determining the carrier frequency change from that at initial application of the device.

Optionally, the extra output signal 334 may provide control by enhancing the electromagnetic field for directed movement of chemical or pharmaceutical molecules in tissue, such as silver ions, for infection control. The enhanced electromagnetic field may be non-uniform in such a way as to direct movement of polar molecules, a method known as dielectrophoresis. Alternatively, the enhanced electromagnetic field may induce an electric field, which directs the movement of ions, a method known as iontophoresis.

An input 332 may be provided to receive external signals, for example, that alter the electromagnetic pulse duration, duty-cycle or pulse repetition rate of the electromagnetic field generated.

Figure 7A:
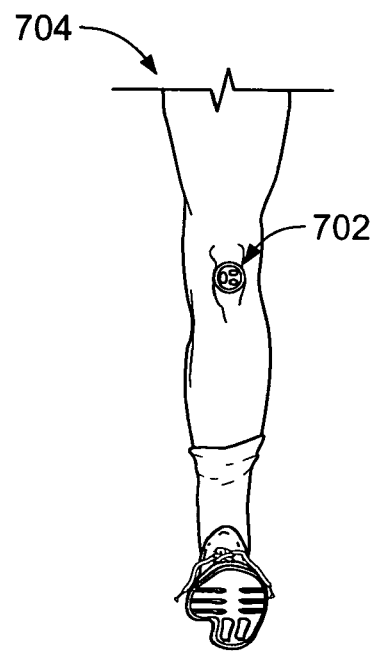
Figure 7B:
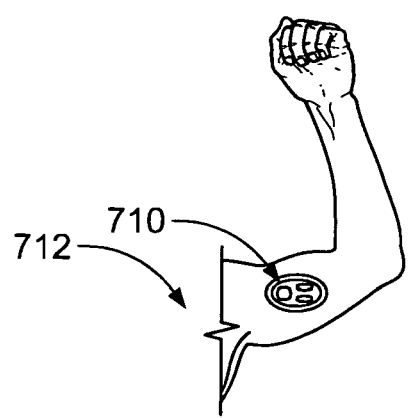
Figure 7C:
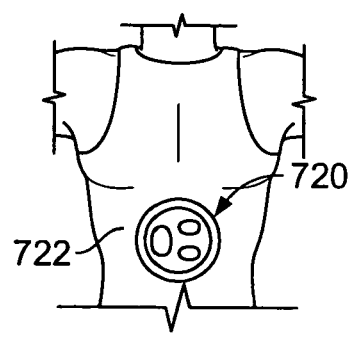
Figure 7D:
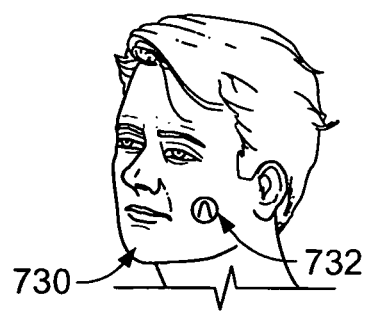

FIGS. 7A-D depict some applications of the therapeutic electromagnetic device. FIG. 7A depicts a therapeutic electromagnetic device affixed to a knee of a human leg 702. The device may be applied to aid in healing of, for example, a cracked knee, a cut, a sprain or strain. FIG. 7B depicts a therapeutic electromagnetic device 710 affixed to a muscle of a human arm 712 to aid in the healing of, for example, a sprain, a strain or a cut. FIG. 7C depicts a therapeutic electromagnetic device 720 affixed to a human abdomen 722 where, for example, lipo-suction procedures were performed. FIG. 7D depicts a human face 730 where a therapeutic electromagnetic device 732 is affixed on a left side of the face to aid in healing of an injury such as a tooth cavity.

FIG. 8 depicts an implementation of an enhanced antenna comprising wires 802 wound around an annular ring 804 mounted on a printed circuit board 810. The ring may be a ferrite or magnetic, electrically-insulating ring. The ring may be arranged to support a battery 806 around the periphery. The battery 806 may be held in place by a retaining clip 808 to retain the battery adjacent the printed circuit board 810. Conductors 812 on the printed circuit board may be arranged to function as a main antenna for the therapeutic electromagnetic device and may be coupled to an electromagnetic field generator (not shown) as described above.

The annular turns of the wires 802 can convey current in phase and frequency with the main antenna 812. The number of turns of wire 802 on the annular ring are arranged to provide a larger magnetic flux than that of the main antenna 812. The windings cause a magnetic flux to enter/exit the outer perimeter of the annular ring. A portion of the (alternating) flux impinges bodily tissue underneath the therapeutic electromagnetic device inducing additional alternating current concentric with the main antenna. The additional induced current may result in magnetic flux that could otherwise be generated by a main antenna having a larger diameter. The magnetic field lines 814 from the main antenna conductors on the printed circuit board will take the path of least magnetic reluctance and pass around the underside of the printed circuit board. Only a weak magnetic field impinges the battery 806. The larger portion of the field may be restrained near the main antenna conductors. The effect is to generate increased magnetic field intensity farther in the bodily tissue. Thus, the main antenna, such as a simple loop antenna, with the enhanced antenna windings on the annular ring can present as an antenna with a larger effective diameter.

A simple loop antenna can produce a near field of electromagnetism, which can be confined within a certain volume by the physical geometry of the antenna. The magnetic field on the axis of a circular loop antenna diminishes in proportion to:

$$MagneticField \approx \frac{1}{\left(1 + \left(\frac{z}{a}\right)^2\right)^{1.5}}$$

where z is the distance from the center of the loop and a is the radius of the loop. Beyond a distance Z, the current induced by the magnetic field in the bodily tissue may be ineffective to provide therapeutic value. The distance Z is measured at the point where the surface of the volume intersects the axis. A therapy volume wherein the electromagnetic field induced in the bodily tissue is adequate to have therapeutic value can be determined from the radius, and circularity, of the loop antenna and the current flowing in the antenna. Outside of this volume, therapy may be inadequate. Inside this volume, therapy may be effective and diminishing on approach to the surface of the therapy volume. In some embodiments, the device effects a penetration of induced current into the bodily tissue such that a therapeutic response is elicited at a depth of at least 2 cm in the bodily tissue.

A larger effective diameter antenna can increase the magnitude of the induced current and extend the depth of penetration of induced current. Hence, the main antenna with the enhanced antenna may result in current induction inside the bodily tissue over a larger area and to a greater depth than with the main antenna alone.

Method of Using Pulsed Electromagnetic Field (PEMF) Therapy in Certain Diseases

Bone and Joint Disorders: The urine of patients with bone and joint disorders typically shows elevated levels of hydroxyproline, hexosamine, creatinine, and uronic acid as a result of metabolic errors in connective tissues surrounding the affected site. Not only can these errors be corrected with PEMF therapy, but joint pain and swelling can be reduced and mobility of the joint increased. Another major advantage of PEMF therapy is that it significantly reduces the time required to heal fractured bones. It has also proven to be effective for osteomyelitis, osteoarthritis, rheumatoid arthritis, cervical spondylosis, and lower back pain (including that caused by disc displacement).

Diabetes Mellitus: Blood sugar levels may be slowly reduced to normal or near normal with application of a pulsed electromagnetic field (PEMF). Although the mechanism of action is not completely understood, the evidence obtained thus far indicates that the procedure not only increases the metabolism of glucose in the tissues but also increases the production of insulin and enhances insulin binding to its specific receptors. The therapy has also proven to be effective for gastritis, peptic ulcer, ulcerative colitis, irritable colon, and hemorrhoids.

Bronchial Asthma: Bronchiolar obstruction can be gradually reduced with PEMF treatment, which liquifies the mucous and facilitates spontaneous clearance. PEMF therapy also has anti-inflammatory action, which helps to ensure that the airways remain free and functional. In patients who have undergone the treatment, Forced Vital Capacity, Forced Expiratory Volume, and Peak Expiratory Flow Rates have increased and wheezing and dyspnea have significantly improved. The treatment is also effective for the common cold, tonsillitis, sinusitis, chronic bronchitis, bronchiectasis Cardiovascular Diseases: PEMF therapy is useful in the prevention of heart attacks in hypertensive patients. Treatment helps to lower blood cholesterol levels and increase the circulation of blood by centrally mediating vascular dilatation. This is particularly important in preventing platelet aggregation and maintaining adequate oxygenation and nutrition of cardiovascular and other tissues. PEMF therapy also effectively disintegrates atherosclerotic plaques. An additional advantage of the procedure is that it blocks the production of free radicals, which play a major role in cardiovascular damage at the cellular level. Other vascular conditions for which PEMF may be effective are phlebitis, endarteritis, and varicose vein.

Brain and Mind Disorders: Directed through the skull at different points, the PEMF can, by inductive coupling, produce an electric current in specific areas of the brain. It may thus be possible to enhance higher brain functions such as learning, memory, and creative thinking by selective stimulation of certain cells. PEMF may have broad application as the modality of choice for psychological disorders such as depression, aggression, anxiety, and stress as well as for Parkinson's disease, epilepsy, migraine, stroke, Alzheimer's and other degenerative brain disorders. In addition, cerebral palsy, mental retardation, hyperactivity, learning disabilities may be improved by PEMF stimulation of the central nervous system.

PEMF therapy can increase the efficiency of brain cells in synthesizing the neuro-chemicals required for the transmission of impulses or commands at the synaptic level and by improving the electrical activity of these cells. The brain is a neuro-chemical complex. The efficiency of the brain or intellectual capacity of the brain depends upon the efficient performance of the brain cells and production of the chemicals that are called neurotransmitters.

Too much dopamine can result in hyperactivity, while too little can result in uncoordinated movements of the limbs (Parkinsonism). Less acetylcholine, a neuro-chemical, in the brain is a reason for dementia especially of the Alzheimer's type. If the brain cells are stimulated repeatedly, after showing inhibition, they rebound and become more active than prior to stimulation. Since PEMF has the ability to stabilize the genes and prevent the activity of oxygen free radicals formed in the cells, it helps to retard the aging process.

Genitourinary Conditions: PEMF has been successfully used to treat genitourinary conditions such as menstrual irregularity, sterility, endometritis, and endometriosis in women and orchitis, prostatitis, and oligospermia in men.

Preoperative and Prophylactic Therapy: PEMF therapy over the epigastrium can provide increased blood profusion to the body's extremities to reduce the inflammatory response to injury. Preoperative treatment of the surgical site has also been shown to accelerate healing.

Post-Operative Recovery: PEMF or TENS over 1.5 inches above the wrist line may reduce or ease the nausea for post-surgical recovery, motion sickness or other forms of nausea symptoms such as vomiting.

Non-Contacting Induction of Electrical Current in Tissue

Devices described herein can induce current at a high frequency. The amount of current induced by a device is partly proportional to the frequency. Modulating a carrier waveform, such as the pulse modulation of 27+/0.5 Mhz (e.g., 27.1 MHz) in devices described herein, allows a larger current to be produced in a tissue than the pulse modulation waveform alone. The pulse modulation is selected for time and amplitude characteristics appropriate to biological systems. The carrier wave ensures that induced current has a magnitude that is maintained coherently within the pulse modulation. A varying pulse modulation is sustained by a similar magnitude of induced current. Rectification occurring in biological systems, such as across cellular membranes, causes the originating pulse modulation waveform to appear as a low frequency voltage. Membrane capacitance allows induced currents to enter cells much more easily than the pulse modulation waveform would by itself. Shunting of current around cells rather than through the cells is also reduced.

No conductive contact of the device with the tissue is required to induce the electrical current in the tissue. The size of the antenna of the device, being much smaller than a wavelength, ensures that the emission is localized to the treatment area. Accordingly, there is generally little far-field emission that might interfere with, for example, domestic appliances.

The devices described herein generally induce current at a much higher frequency than tissue-stimulating devices such as, for example, inductive bone-healing stimulators that pulse coils to produce a magnetic field or capacitive stimulators that produce a pulsed electric field.

Positioning of Therapeutic Devices

Therapeutic devices such as a PEMF apparatus, a transcutaneous electrical neural stimulator (TENS), or a static magnet array can be positioned at particular points on the body to achieve an enhanced medical therapeutic effect, e.g., accelerate healing, reduce pain, swelling and bruising. TENS operates by causing an electric current to be passed between electrodes placed on the skin over, for example, a painful area. Devices are described herein that can induce electrical current in a bodily tissue without the use of electrodes that are applied to the skin.

A therapeutic device can be positioned and operated at a specific acupuncture point, including but not limited to the following: the external end of the elbow transverse crease; the depression at the lower border of the malleolus lateralis; below (e.g., about 1 inch below) the lateral extremity of the clavicle at the level of the first intercostals space; between the fourth lumbar vertebra and the fifth lumbar vertebra; 1 inch to the right or left (horizontally) of the position between the fourth lumbar vertebra and the fifth lumbar vertebra; a depression anterior or inferior to the head of the fibula; about 1.5 inches above the medial border of the patella; between the radius and the palmaris longus; or at a position of pain (e.g., where the pain sensation is the strongest in an individual). FIG. 9 depicts specific anatomical locations where a therapeutic device described herein can be placed on an individual as part of a treatment program (e.g., a treatment for the reduction or elimination of pain).

The therapeutic devices described herein can be used in combination with specific acupuncture positioning techniques to reduce or eliminate pain. Examples of pain-related disorders include, for example, pain response elicited during tissue injury (e.g., inflammation, infection, and ischemia), pain associated with musculoskeletal disorders (e.g., joint pain such as that associated with arthritis, toothache, and headaches), pain associated with surgery, pain related to irritable bowel syndrome, an chest pain.

Other implementations are within the scope of the following claims.

What is claimed is:

1. A portable, self-contained medical therapeutic device comprising:
   an electromagnetic field generator;
   an antenna coupled to the generator and arranged to radiate the electromagnetic field;
   a battery coupled to the generator;
   an annular ring surrounding the battery;
   a wire wound around the annular ring; and
   an activator to initiate radiation of the electromagnetic field,
   wherein the device is adapted to be disposed over a bodily tissue to induce an alternating current in the bodily tissue and promote at least one of communication between cells or cellular stimulation.

2. The device of claim 1, wherein the antenna comprises antenna conductors on a printed circuit board.

3. The device of claim 1, wherein the annular ring has a stepped cross-section and wherein the wire wound on a top and outer side of the annular ring is coupled to the antenna conductors.

4. The device of claim 1, wherein the annular ring comprises a ferrite ring.

5. The device of claim 1, wherein the annular ring comprises an insulating-magnetic ring.

6. The device of claim 1, wherein the alternating current induced in the bodily tissue is parallel or perpendicular to the direction of antenna conductors.

7. A method of inducing electrical current in a bodily tissue, the method comprising:
   positioning the device of claim 1 adjacent a bodily tissue of an individual; and
   operating the device for a duration, at a frequency, and at a peak available radiated power density effective to induce electrical current in the bodily tissue, wherein the device is positioned relative to the individual such that the device induces electrical current in the bodily tissue without making conductive contact with the bodily tissue.

8. The method of claim 7, wherein operating the device comprises causing radiation of a pulsed electromagnetic field having a frequency of 27+- 0.5 MHz.

9. The method of claim 7, wherein operating the device comprises causing radiation of an electromagnetic field having a peak available radiated power density of less than 100 microwatts per square centimeter measured at the surface of the bodily tissue.

10. The method of claim 7, further comprising reducing a pain sensation in the individual with the induced electrical current.

11. The method of claim 7, wherein positioning the device comprises positioning a delivery system.

12. The method of claim 11, wherein positioning the delivery system comprises positioning a patch, bandage, pad, brace, strap, tape, adhesive, or cast.

13. The method of claim 11, wherein positioning the delivery system comprises positioning a single use adhesive bandage.

14. The method of claim 7, further comprising pulsing the generated electromagnetic field.

15. The method of claim 14, further comprising altering at least one of a duty-cycle and a pulse repetition rate of the pulsed electromagnetic field.

16. The method of claim 15 further comprising altering the duty cycle between approximately 8%-10%.

17. The method of claim 7 further comprising operating the device for a duration, at a frequency, and at a peak available radiated power density effective to elicit a therapeutic response in the individual.

18. The method of claim 7, further comprising reducing pain associated with a pain-related disorder in the individual with the induced electrical current.

19. The method of claim 7, further comprising reducing inflammation in a bone, joint, soft-tissue, or connective tissue disorder in the individual with the induced electrical current.

20. The method of claim 7, further comprising reducing pain associated with a bone, joint, soft-tissue, or connective tissue disorder in the individual with the induced electrical current.

21. The method of claim 7 further comprising reducing pain associated with a dental condition in the individual with the induced electrical current.

22. The method of claim 7 further comprising reducing pain associated with an arthritic disorder.

23. The method of claim 7 further comprising reducing pain associated with osteoarthritis of the with the induced electrical current.

24. The method of claim 7 further comprising reducing nausea and vomiting associated with post-surgical recovery, chemotherapy, or motion sickness with the induced electrical current.

25. A method of treating an individual, the method comprising:
providing a device comprising an electromagnetic field generator, a battery coupled to the generator, and an annular ring surrounding the battery;
positioning the device adjacent a bodily tissue of an individual; and
operating the device for a duration, at a frequency, and at a peak available radiated power density effective to elicit a therapeutic response in the individual,
wherein the device is positioned relative to the individual such that the device induces electrical current in the bodily tissue of the individual without making conductive contact with the bodily tissue, and wherein the device effects a penetration of the induced current into the bodily tissue such that the therapeutic response is elicited at a depth of at least 2 cm in the bodily tissue.

26. The method of claim 25 further comprising eliciting the therapeutic response at a depth of at least 3 cm in the bodily tissue.

27. The method of claim 25 further comprising eliciting the therapeutic response at a depth of 2 to 3 cm in the bodily tissue.

28. The method of claim 25 further comprising reducing pain associated with a pain-related disorder in the individual with the induced electrical current.

29. The method of claim 25 further comprising reducing inflammation associated with a bone, joint, soft-tissue, or connective tissue disorder in the individual with the induced electrical current.

30. The method of claim 25 further comprising reducing pain associated with a bone, joint, soft-tissue, or connective tissue disorder in the individual with the induced electrical current.

31. The method of claim 25 further comprising reducing pain associated with a dental condition in the individual with the induced electrical current.

32. The method of claim 25 further comprising reducing pain associated with an arthritic disorder in the individual with the induced electrical current.

33. The method of claim 25 further comprising reducing pain associated with osteoarthritis of the knee in the individual with the induced electrical current.

34. A method of treatment, the method comprising:
providing a device selected from the group consisting of a pulsed electromagnetic field therapy (PEMF) apparatus, a transcutaneous electrical neural stimulator (TENS), and a static magnet array;
positioning the device at a distance from an individual effective to elicit a therapeutic response in the individual, wherein the device is positioned at a bodily location selected from the group consisting of the external end of the elbow transverse crease, the depression at the lower border of the malleolus lateralis, below the lateral extremity of the clavicle at the level of the first intercostals space, between the fourth lumbar vertebra and the fifth lumbar vertebra or 1 inch to the right or left thereof horizontally, a depression anterior or inferior to the head of the fibula, about 1.5 inches above the medial border of the patella, and between the radius and the palmaris longus; and
maintaining the device at the bodily location for a duration effective to elicit the therapeutic response;
wherein the therapeutic response includes the reduction of pain.

35. The method of claim 34 further comprising reducing pain associated with a disorder selected from the group consisting of adhesive capsulitis, tennis elbow, osteoarthritis, back pain, multiple sclerosis, tendon inflammation, and carpal tunnel syndrome.

36. The method of claim 34, wherein the device is a PEMF apparatus.

37. The method of claim 34, wherein the device is a TENS.

38. The method of claim 34, wherein the device is a static magnet array.

39. The method of claim 34, wherein the device comprises:
an electromagnetic field generator;

an antenna coupled to the generator and arranged to radiate the electromagnetic field;
a power source coupled to the generator;
an annular ring surrounding the power source;
a wire wound around the annular ring; and
an activator to initiate radiation of the electromagnetic field,
wherein the device is self-contained and portable.

* * * * *